United States Patent [19]
Van Oeveren et al.

[11] Patent Number: 6,087,120
[45] Date of Patent: Jul. 11, 2000

[54] MEASUREMENT OF COMPLEMENT ACTIVATION BY BIOMATERIALS BY MEANS OF COMPLEMENT CONVERTASE CLEAVAGE OF PEPTIDE SUBSTRATES

[75] Inventors: Willem Van Oeveren, Zuidwolde, Netherlands; Jacob De Haan, Adlkofen, Germany

[73] Assignee: HaemoProbe B.V., Netherlands

[21] Appl. No.: 09/101,973

[22] PCT Filed: Feb. 3, 1997

[86] PCT No.: PCT/NL97/00030

§ 371 Date: Mar. 8, 1998

§ 102(e) Date: Mar. 8, 1998

[87] PCT Pub. No.: WO97/28276

PCT Pub. Date: Aug. 7, 1997

[30] Foreign Application Priority Data

Feb. 2, 1996 [EP] European Pat. Off. ............... 96200233

[51] Int. Cl.⁷ ....................................................... C12Q 1/37
[52] U.S. Cl. ................................................................ 435/23
[58] Field of Search .................................................. 435/23

[56] References Cited

FOREIGN PATENT DOCUMENTS

| | | |
|---|---|---|
| 57-075956 | 5/1982 | Japan . |
| 57-075957 | 5/1982 | Japan . |
| 57-075958 | 5/1982 | Japan . |
| 91/12338 | 8/1991 | WIPO . |

OTHER PUBLICATIONS

Labarre et al., "Strategy for in vitro Evaluation of the Interactions Between Biomaterials and Complement System", J. Appl. Biomat., vol. 4, No. 3, pp. 231–240, 1993.

Primary Examiner—Jon P. Weber
Attorney, Agent, or Firm—Varnum, Riddering, Schmidt & Howlett, LLP

[57] ABSTRACT

A process for determining complement activation due to contact between a biomaterial and a complement system, by incubating in vitro the biomaterial with the complement system and determining the formation of a complement convertase by using a substrate of the complement convertase and detecting substrate cleavage. The biomaterial after said incubation with the complement system may be separated therefrom and formation of a complement convertase may be determined with the separated biomaterial, the separated complement system, or both. The complement convertase may be Factor B convertase, C3 convertase or C5 convertase, and the substrate may be a labeled oligopeptide comprising an amino acid sequence corresponding to the cleavage site of the complement convertase. Suitable labels are dyes, fluorochromes, radioactive atoms or groups, and enzymes. Either classical or alternative pathway complement activation, or both, are determined. The complement system may be a non-clotting derivative of blood, blood plasma or blood serum, including fibrinogen depleted forms, anticoagulated forms, and derivatives containing thrombin inhibitor. Complement convertase substrates suitable for use in the process are also disclosed.

12 Claims, 8 Drawing Sheets

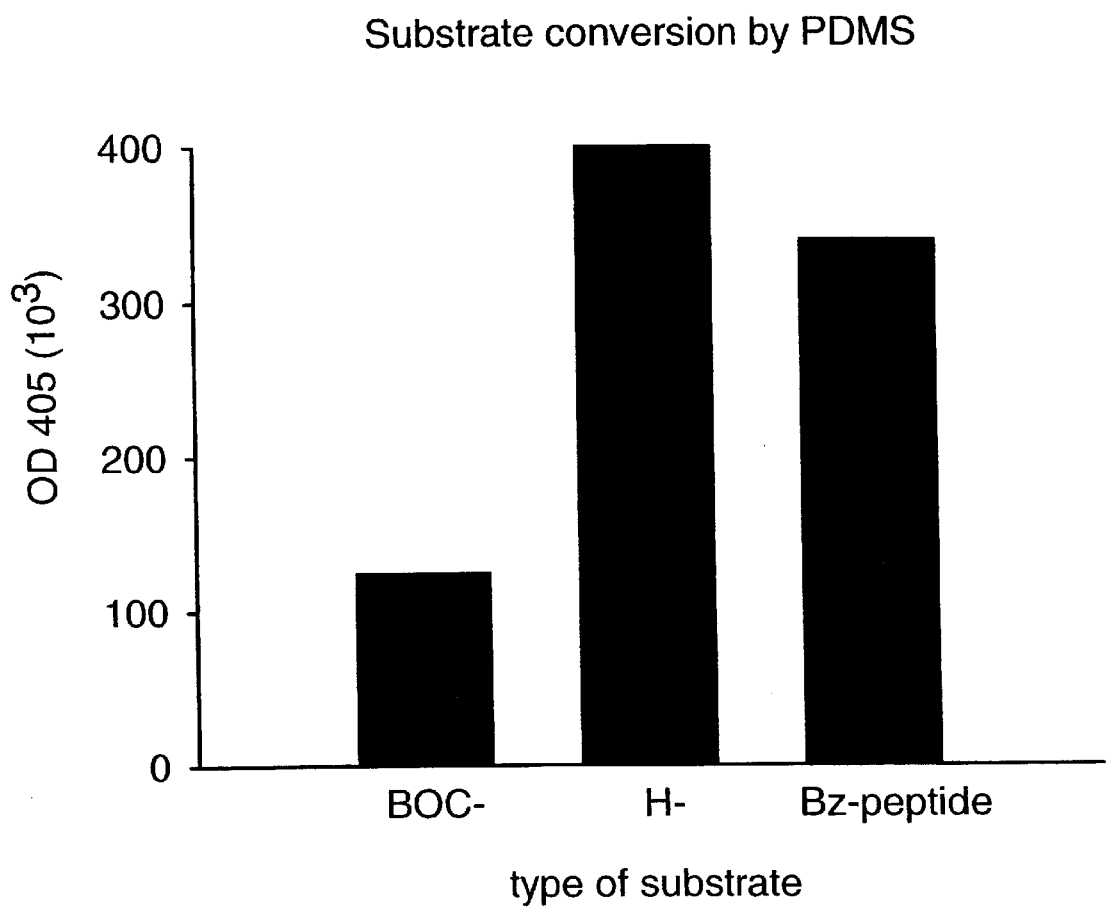
FIGURE 3-A

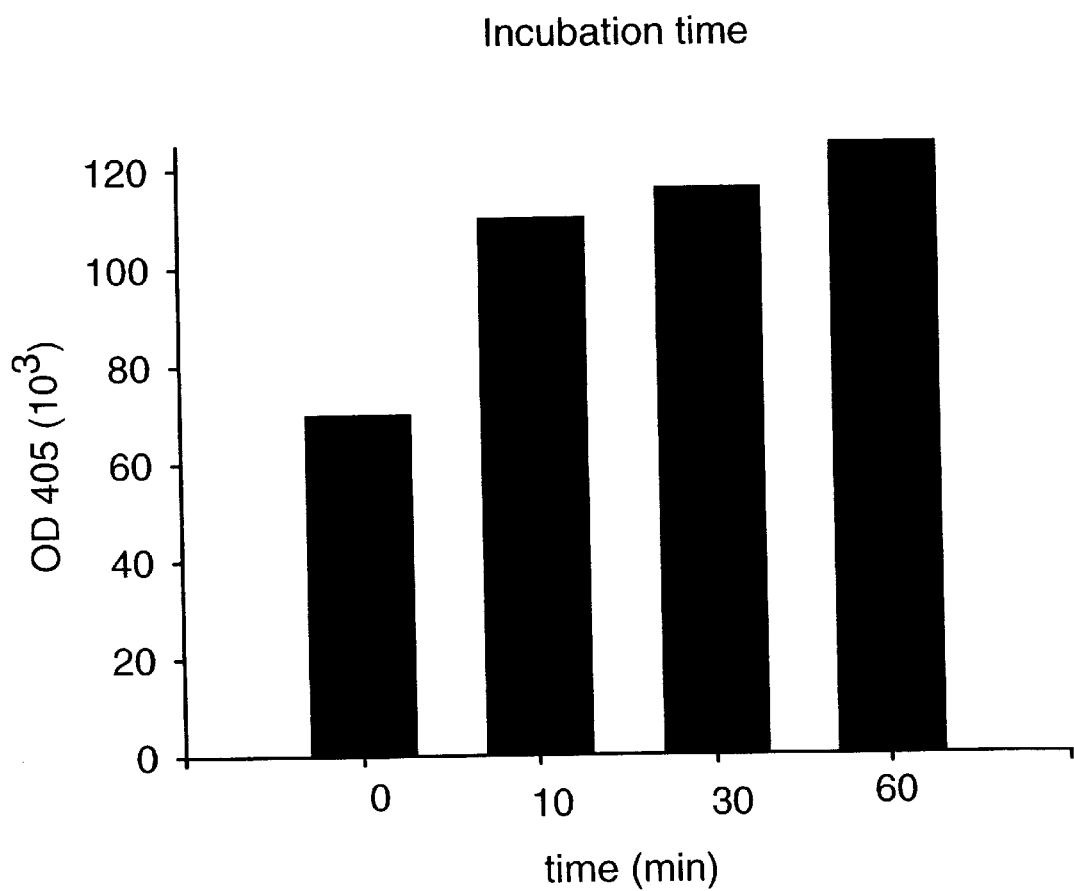
FIGURE 3-B

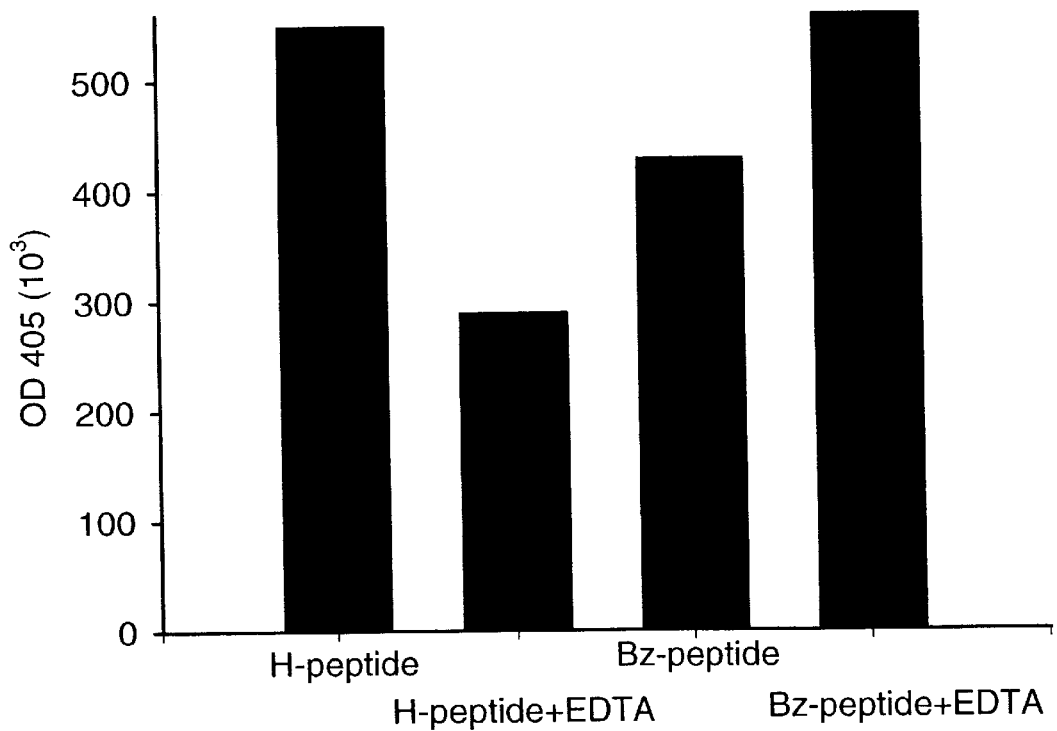
FIGURE 4-A

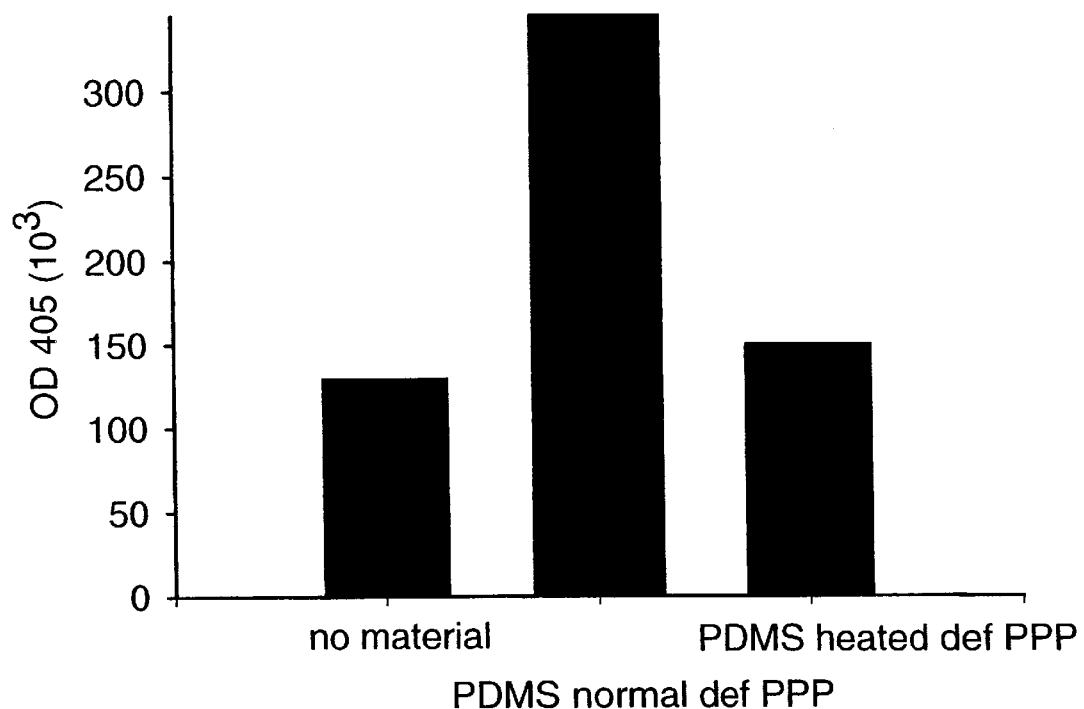
FIGURE 4-B

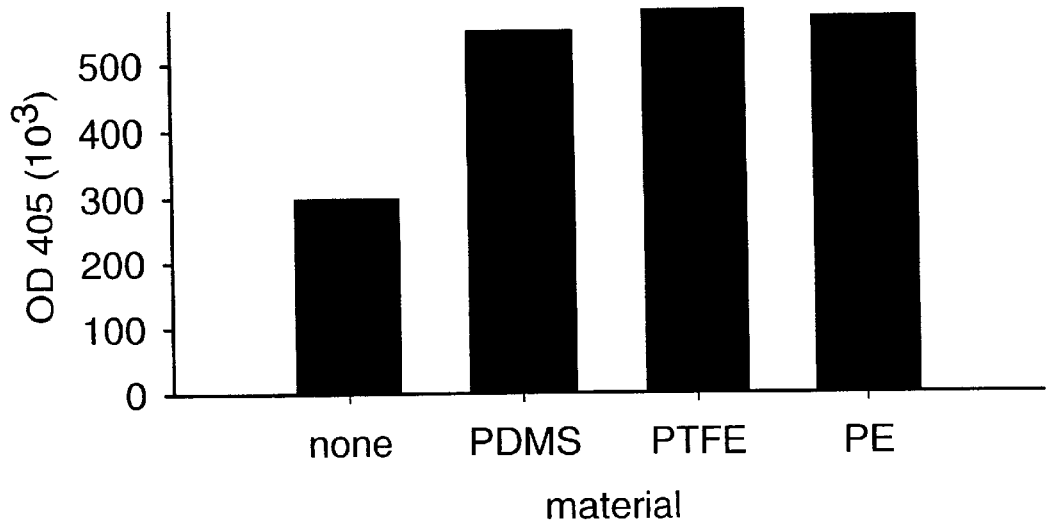
FIGURE 5-A
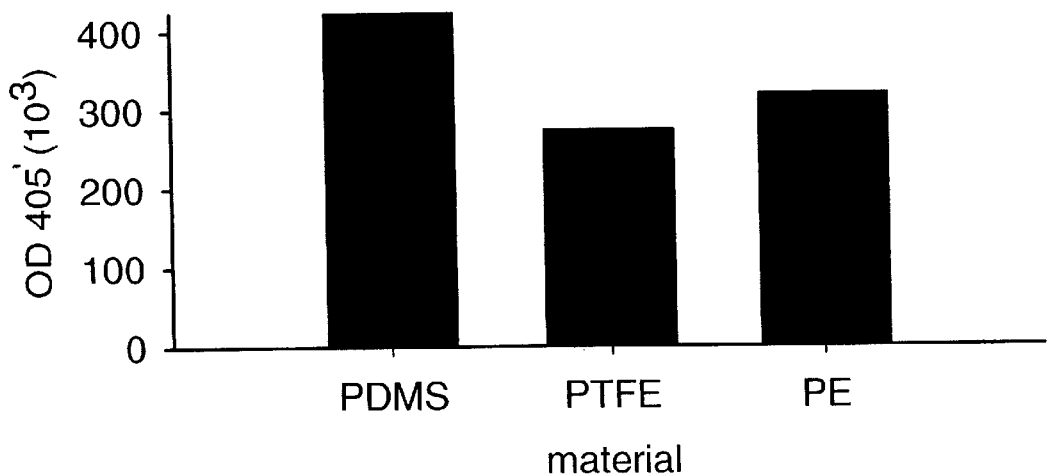
FIGURE 5-B

MEASUREMENT OF COMPLEMENT ACTIVATION BY BIOMATERIALS BY MEANS OF COMPLEMENT CONVERTASE CLEAVAGE OF PEPTIDE SUBSTRATES

This is a U.S. National Phase Application of Application No. PCT/NL97/00030, filed Feb. 3, 1997, based on European Application No. 962002333, filed Feb. 2, 1996.

TECHNICAL FIELD

The invention is in the field of diagnostics and relates to a new diagnostic technique in medicine. More specifically it is concerned with the measurement of activation of an immunologic system in blood, the complement system, when blood is contacting a foreign body surface (biomaterial).

BACKGROUND OF THE INVENTION

Medical devices are frequently used in contact with blood in blood banks, cardiovascular applications, organ replacement and vascular surgery. These devices are made from plastics, metals or modified tissue and have in common that they activate the natural host defence mechanism of blood by a foreign body reaction (FIG. 1). One of the direct effects of blood with such a foreign surface is clotting, which is prevented by anticoagulants. The other effect is activation of the immune system, which cannot be prevented pharmacologically.

This immune response is effected by the complement system, a number of serum proteins consisting of components, activators, stabilizers and inhibitors. The complement system initiates chemotaxis and activation of leucocytes, is essential for phagocytosis of microorganisms and is capable of killing bacteria directly by inducing cell lysis. An implanted foreign body surface could also be attacked by the complement system. In view of the wide-reaching biologic effects of the complement system, the consequences of uncontrolled complement activation would be devastating (1–4). Continued activation of the sequence attracts leukocytes which release lysosomal enzymes as a byproduct of phagocytosis, which in turn cause necrosis of normal tissue (5–8).

Normally, tight controls are in effect which regulate the complement system to protect host tissue. The cascade is naturally moderated by the instability of the enzymes formed. Once a component is activated, failure to combine with its substrate within milliseconds cause it to decay. In addition, several plasma inhibitors are present to control the cascade. However, during the use of medical devices these regulatory mechanisms appear often inadequate due to the unnatural surface. Therefore, testing of complement activation by materials used for the construction of medical devices is needed to ensure the use of materials with as low complement activation as possible.

THE COMPLEMENT SYSTEM (FIG. 2)

Activation of the complement system can occur via two distinct routes—the classical and the alternative pathway. The end result of complement activation is cytolysis, although this is probably not the major function of complement. In the course of complement activation, biologically active factors are released. These factors enhance the immune response by directing neutrophil migration, promoting immune adherence, increasing vascular permeability, and interacting with other inflammatory systems.

The classical pathway components are designated C1g, C1r, C1s, C4, C2, C3, C5, C6, C7, C8, C9. The alternative pathway components are designated Factor B, Factor D, Properdin, H and I.

Initiation of the classical pathway begins when antibody binds antigen. C1g binds the altered Fc region of IgG or IgM that has bound antigen. Upon binding, C1r activates C1s which initiates the activation unit by cleaving a peptide from both C4 and C2. C1s thus cleaves C4 into C4a and C4b and C2 into C2a and C2b. C2a binds to C4b forming C4b2a. C4b2a, the C3 convertase, is a proteolytic enzyme. It cleaves C3 into C3b, which may bind to the activating surface, and C3a which is released into the fluid phase (9). C3 convertase has the ability to cleave many C3 molecules. This could result in the deposition of a large number of C3b molecules on the activating surface. However, due to the labile nature of C3b, very few molecules actually bind. C4b2a3b, the C5 convertase, is formed when C3 is cleaved. C5 convertase, also an enzyme, can cleave many C5 molecules into C5a and C5b.

The alternative pathway provides natural, non-immune defense against microbial infections. In addition, this pathway amplifies antibody-antigen reactions.

Alternative pathway recognition occurs in the presence of C3b and an activating substance such as bacterial lipoprotein, surfaces of certain parasites, yeasts, viruses and other foreign body surfaces, such as biomaterials (10–15). C3b originates from classical pathway activation and/or from natural spontaneous hydrolysis of C3. The resulting C3b binds to the surface of the activating substance. In the presence of magnesium, Factor B binds to the C3b which is bound to the activating surface (16,17). Factor D then cleaves B, releasing the Ba fragment and forming C3bBb. Properdin stabilizes the C3bBb complex and protects it from decay. C3bBbP is the alternative pathway convertase. It also has the ability to cleave many C3 molecules. Cleavage of C3 results in the formation of C3bBb3b, the C5 convertase (18,19). This enzyme is also stabilized by P to form C3bBb3bP. C5 convertase can cleave many molecules of C5 into C5a and C5b.

The complement system has a positive feedback mechanism that amplifies activation. C3b produced from either pathway interacts with Factors B, D and P from the alternative pathway (20). This interaction creates additional C3 convertase to activate the membrane attack complex.

The membrane attack complex is common to both pathways. It begins with the cleavage of C5 by C5 convertase generated during either classical or alternative pathway activation. When C5 is cleaved, C5a is released into the fluid phase while C5b attaches to the activating surface at a binding site distinct from that of C3b. One molecule each of C6 and C7 binds to C5b to form a stable trimolecular complex to which C8 binds. Then, up to 6 molecules of C9 can bind to C8 enhancing the effectiveness of the attack complex to induce membrane damage if the activating surface is a microorganism.

The significance of complement activation is not limited to membrane damage resulting from the attack complex. The active peptides released in the course of complement activation contribute to the immune response by increasing vascular permeability and contraction of smooth muscle, promoting immune adherence, granulocyte and platelet aggregation, enhancing phagocytosis, and directing the migration of neutrophils (PMN) and macrophages to the site of inflammation (21–24).

The cleavage of C3 and C5 results in the release of two small biologically active peptides, C3a and C5a. The peptides act as anaphylatoxins. They amplify the immune response by causing the release of histamine, slow releasing substance of anaphylaxis (SRS-A), and heparin from basophils and mast cells. These substances increase capillary permeability and contraction of smooth muscle resulting in edema and inflammation (25–27).

In addition to its role as an anaphylatoxin, C5a is a potent chemotactic factor. This mediator causes the directed migration of PMN and macrophages to the site of inflammation so these leukocytes will phagocytize and clear immune complexes, bacteria and viruses from the system.

In a process known as immune adherence, C3b or C4b deposited on a soluble immune complex or surface permit binding of complement receptors on PMN, macrophages, red blood cells and platelets (28,29). In these cases C3b and C5b are considered opsonins as their presence results in more effective phagocytosis.

LABORATORY MEASUREMENT OF COMPLEMENT PROTEINS

The following two techniques for assessing the complement system are known.
1) Hemolytic techniques measure the functional capacity of the entire sequence—either the classical or alternative pathway.
2) Immunological techniques measure the protein concentration of a specific complement component or split product.

HEMOLYTIC TECHNIQUES

In order for lysis to occur in a hemolytic technique, all of the complement components must be present and functional. Therefore hemolytic techniques can screen both functional integrity and deficiencies of the complement system (30,31).

To measure the functional capacity of the classical pathway, sheep red blood cells coated with hemolysin (rabbit IgG to sheep red blood cells) are used as target cells (sensitized cells). These Ag-Ab complexes activate the classical pathway and result in lysis of the target cells when the components are functional and present in adequate concentration. To determine the functional capacity of the alternative pathway, rabbit red blood cells are used as the target cell.

The hemolytic complement measurement is applicable to detect deficiencies and functional disorders of complement proteins, since it is based on the function of complement to induce cell lysis, which requires a complete range of functional complement proteins. The so-called CH50 method, which determines classical pathway activation, and the AP50 method for the alternative pathway have been extended by using specific isolated complement proteins instead of whole serum, while the highly diluted test sample contains the unknown concentration of the limiting complement component. By this method a more detailed measurement of the complement system can be performed, indicating which component is deficient.

However, in order to induce deficiencies of complement proteins in serum from healthy individuals, which must be used to determine biocompatibility, a very high extent of complement activation and consumption is required. Therefore, in general the hemolytic techniques are not sensitive enough to detect complement activation by biomaterials. Some hemolytic techniques based on isolated components with a highly diluted test sample appeared to be more sensitive, but even complement activation induced by 5 $m^2$ surface of a heart-lung machine could marginally be detected with these methods (32).

IMMUNOLOGIC TECHNIQUES

Polyclonal antibodies were raised against different epitopes of the (human) C3, C4 an C5 complement factor. With these antibodies radioimmunoassays were developed against the minor split products of these complement factors, which are particularly performed after precipitation of the native factor (33–36). Binding of the antibody with the split product in competition with a known concentration of labeled split product could then be measured. Later on also (monoclonal) antibodies were raised to epitopes of the split products, rendering a higher specificity. Nowadays, radio-immunoassays, ELISA's and radial diffusion assays are available to detect complement split products.

In contrast to the hemolytic techniques, immunologic techniques provide a high sensitivity to detect complement activation, since they allow measurement of split-product formation, while these split products are only found at very low concentrations in blood from healthy individuals. Thus, clinically the measurement of the soluble split products C3a, C4a and C5 a in blood plasma has allowed a more distinct evaluation of complement activation in patients (37). Later on the soluble form of the terminal complex (SC5b-9) was found a sensitive marker of complement activation (38). For detection of in vivo complement activation these techniques are most suitable, particularly since blood samples can be collected in medium containing inhibitors of the complement system. Thus only the complement activation formed in vivo is measured in the subsequent assay.

However, these in vivo or clinical studies cannot be used to determine the biocompatibility of biomaterials. Main problem during clinical use is that during application of biomaterials the complement system is activated by a variety of material-independent factors, such as surgical damage of tissue, ischemia, blood-air contact, endotoxin and drugs which alltogether dominate complement activation induced by the biomaterial. Thus, for pure biocompatibility testing in vitro studies are required, based on exposure of the biomaterial to isolated blood or blood components (usually plasma or serum). At this end difficulties arise. Starting with the isolation of blood from a donor, during preparation of plasma or serum for the test, and during the test phase itself in the test tube the complement system is activated and high concentrations of split products are formed in plasma or serum. This high concentration of split products dominates the split products eventually formed by the test biomaterials during the test procedure. Thus, the sensitive immunologic techniques appear unsuitable for in vitro testing of biocompatibility. Moreover, it has been shown that to some biomaterials the split products adsorb to the surface. By the immunologic techniques these adsorbed split products are not detected. This leads to false negative appreciation of the test sample.

SUMMARY OF THE INVENTION

The invention provides a process for determining complement activation due to contact between a biomaterial and a complement system, comprising incubating in vitro the biomaterial with the complement system and determining the formation of a complement convertase by using a substrate of the complement convertase and detecting cleavage of said substrate. Preferably the biomaterial after said incubation with the complement system is separated therefrom and the determination of the formation of a complement convertase is carried out with the separated biomaterial, the separated complement system, or both.

The term "biomaterial" as used herein refers generally to any material, or product made thereof, which could come (or be brought) into contact with biological fluids such as blood and may or may not activate complement.

Preferably, the complement convertase is selected from the group consisting of Factor B convertase, C3 convertase and C5 convertase. More preferably, the complement convertase is C5 convertase.

Although in principle any complement convertase substrate and any detection method of cleavage of said substrate can be used, it is preferred that the complement convertase substrate is a labeled oligopeptide comprising an amino acid sequence corresponding to the cleavage site of the complement convertase. More preferably the labeled oligopeptide is a labeled tripeptide having the general formula Leu-Gly-Arg-Label, or Leu-Ala-Arg-Label, or Gln-Lys-Arg-Label, wherein Label represents the label and the terminal amino group of the N-terminal amino acid may be blocked. The label in said labeled oligopeptide may be selected from the group consisting of dyes, fluorochromes, radioactive atoms or groups, and enzymes, and preferably is a label which becomes (more easily) visible or detectable after cleavage of the complement convertase substrate.

The process may be carried out in such a way that either classical pathway complement activation, alternative pathway complement activation, or both, are determined. Proper selection of reaction conditions, such as temperature, or the presence of a particular kind of metal ions ($Ca^{++}$ or $Mg^{++}$ ions), or directed suppression of a chosen pathway (e.g. using antibodies effective for that purpose) can be used to restrict the test to a selected complement activation pathway.

The complement system used in the process may be any fluid containing constituents of the complement system. In case the process is used to determine biocompatibility of a biomaterial, the complement system used must contain an effective complement system, at least an active classical pathway complement system, an active alternative pathway complement system, and preferably both. The complement system used may be an artificial system, or a natural or semi-natural complement system, such as preferably a non-clotting derivative of blood, blood plasma or blood serum, including fibrinogen depleted forms, anticoagulated forms, and derivatives containing thrombin inhibitor.

Interference by other enzymes than the relevant complement convertase may be reduced by carrying out the incubation of biomaterial and complement system and/or the substrate cleavage step in the presence of inhibitors of said other enzymes.

The aim of the process may be to determine the complement activating properties of a biomaterial, in which case the complement system will usually be derived from blood known to have an active classical pathway complement system, an active alternative pathway complement system, or both, such as pooled normal blood.

Alternatively, the aim of the process may be to determine the complement response properties of a complement system, such as the blood of a patient suspected of having a complement deficiency, in which case biomaterials with known complement activating properties are used.

The invention furthermore relates to complement convertase substrates for use in a process as defined herein, in particular a labeled oligopeptide comprising an amino acid sequence corresponding to the cleavage site of a complement convertase, more particularly a labeled tripeptide having the general formula Leu-Gly-Arg-Label, or Leu-Ala-Arg-Label, or Gly-Lys-Arg-Label, wherein Label represents the label and the terminal amino group of the N-terminal amino acid may be blocked.

BRIEF DESCRIPTION OF THE DRAWINGS

FIG. 3a shows the substrate conversion results after incubation of polydimethylsiloxane (PDMS) in fibrinogen-depleted plasma (def PPP) for different substrates. After incubation of PDMS in def PPP, the washed PDMS was incubated in BOC-Leu-Gly-Arg-pNA solution while def PPP was mixed with H-Leu-Gly-Arg-pNA or Bz-Leu-Gly-Arg-pNA. Results are corrected for background colour. Enzymatic activity was formed as shown by cleavage of the R-Leu-Gly-Arg-pNA substrates. The substitution of R with BOC was most effective on the PDMS surface, H- and Bz-substitution were effective in the plasma solution.

FIG. 3b shows the convertase activity formed onto the PDMS surface during incubation at variable times in plasma. The PDMS was incubated at a variable time in def PPP, washed and then subjected to BOC-Leu-Gly-Arg-pNA.

FIG. 4a shows the effect of ethylenediamine tetra-acetic acid (EDTA) during substrate cleavage. According to the protocol PDMS was incubated in defibrinated plasma and then removed. H- or Bz-substrate was then added to the plasma and incubated for 60 hours to develop colour. During this second incubation new complement convertases could be formed, unless EDTA was added. EDTA did not prevent substrate cleavage by formed complexes. Cleavage of Bz-Leu-Gly-Arg-pNA was not reduced by EDTA, which indicates aspecificity of this substrate.

FIG. 4b shows the effect of heating defibrinated plasma prior to the incubation. Def PPP was heated for 30 min at 56° C. before PDMS was incubated therein. Factor B from the alternative complement pathway is known to denaturate at temperatures above 56° C. By treatment of plasma at that temperature the alternative pathway of complement becomes afunctional. If PDMS was incubated in heated plasma no further activation of the complement system was observed.

FIGS. 5a, 5b show the effect of different materials. PDMS (polydimethylsiloxane), PTFE (polytetrafluoroethylene) and PE (polyethylene) all showed binding of convertase on the surface (FIG. 5a, using BOC-Leu-Gly-Arg-pNA as substrate) and release in the incubation plasma (PPP) solution (FIG. 5b, using H-Leu-Gly-Arg-pNA as substrate). With the present test conditions the measurement in plasma appeared most discriminative between the materials, showing PDMS as most activating.

DETAILED DESCRIPTION OF THE INVENTION

Figure 1:
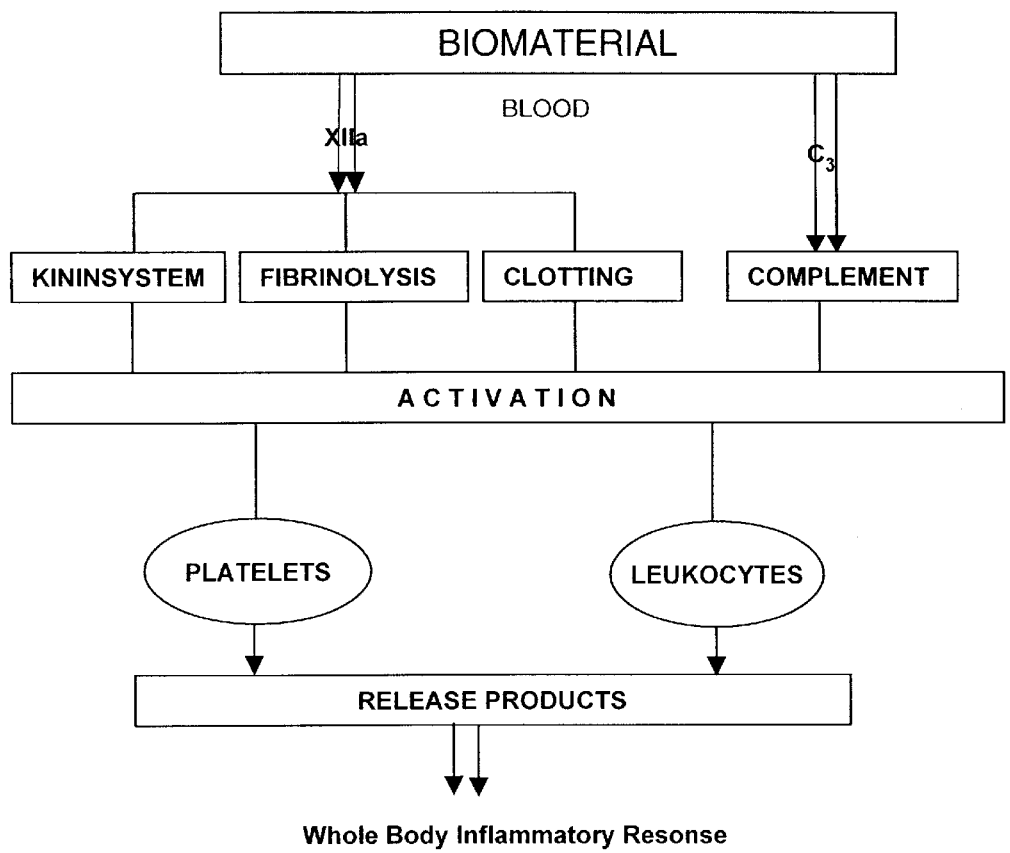
FIG. 1 shows schematically the interaction between blood and a foreign biomaterial. When blood is exposed to biomaterial, the contact system (Factor XII and cofactors) as well as the complement system (C3) will be activated. The contact system leads to further activation of the kinin, fibrinolytic and clotting system. Activation of the complement system leads to generation of chemotactic and membrane attack complement peptides. The products generated trigger platelets and leucocytes to release enzymes. If this process escapes the natural control, a whole body inflammatory response may induce severe illness to patients.
Figure 2:
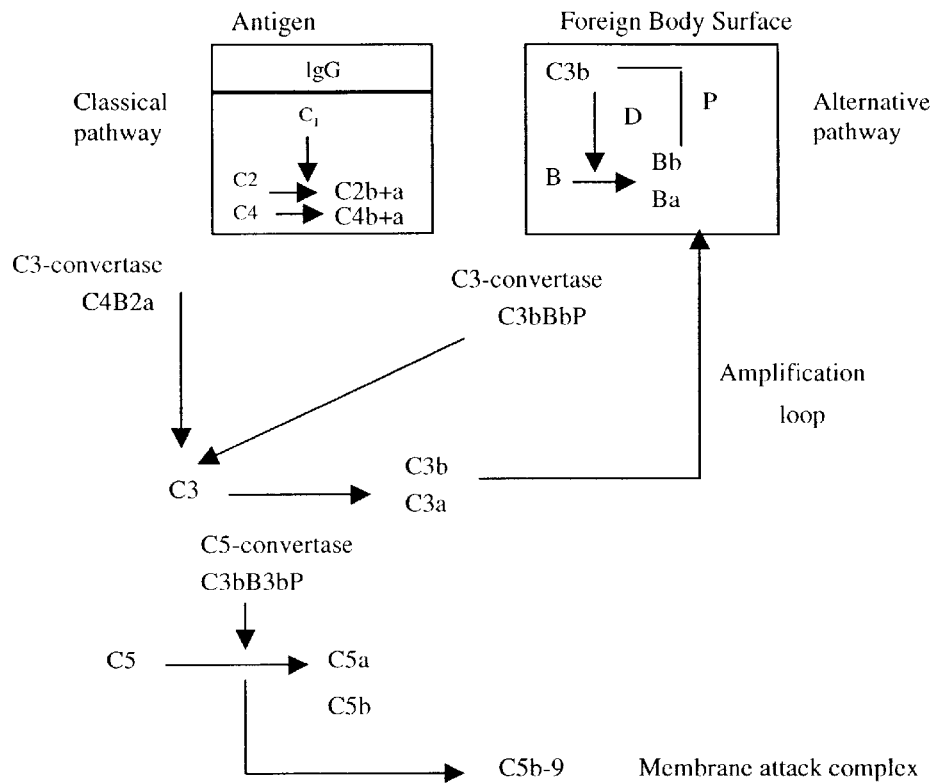
FIG. 2 shows schematically the classical and alternative pathways of the complement system. The complement system is initiated through the classical or alternative pathway. The classical pathway components C1, C2 and C4 are in particular formed after antibody-antigen recognition, the alternative pathway is initiated by C3b binding and stabilization of C3Bb by factors P and D on any foreign body surface, such as biomaterials. After C3 cleavage by this convertase, newly formed C3b will then bind to the target surface, thus amplifying the reaction. By both pathways C3 and subsequently C5 is cleaved by the respective convertases and the membrane attack complex is formed onto the target surface as well as soluble in blood. C3a and C5a fragments are chemotactic and activating for leucocytes.

The subject invention provides an enzymatic technique to determine convertase activity towards synthetic peptides, which results in release of a labelling substance, such as a chromogenic, fluorescent, or radioactive label.

Although the complement system is activated through enzymatic cleavage of Factors B, C3 and C5 by convertases, these enzymes have not yet been considered as useful markers for complement activation due to their intrinsic lability, short half life, but most of all due to their aspecific nature (39–42). Therefore it was a surprise to observe remaining activity of these convertases on the surface of materials, as well as in the fluid phase, which could be ascribed to complement convertase activity by using inhibitors of other potential substrate cleaving enzymes.

The amino acid sequence of the natural substrates for the complement convertases (Factors B, C3, C5) is known. Also the cleavage site of Factor B by the Factor B cleaving enzyme C3bD, of C3 by the C3convertases (C4b2a and C3bBbp) and of C5 by the C5 convertase (C3bBb3bP) is known (43,44). Thus an artificial substrate resembling these structures could be used for these enzymatic processes. These small peptides substrates can be labeled in different ways (45,46) to measure the cleavage by the corresponding convertase activity. A suitable labeled peptide substrate for C3-convertase would be Leu-Ala-Arg-pNA, for C5-convertase Leu-Gly-Arg-pNA, and for Factor B-convertase Gly-Lys-Arg-pNA. The nature of the label is not critical, and the amino group of the N-terminal amino acid may be free (H-form) or blocked (e.g. by BOC or Bz).

The new enzymatic technique is based on the convertases formed on the surface of the test material and detects these convertases bound to the surface and/or free in plasma. Specifically for the bound complement proteins this technique is most suitable, in contrast to the hemolytic and immunologic techniques. The new enzymatic technique shares the advantage of the hemolytic techniques in being relevant to the real activity of complement, since it measures important steps in the cascade. Also the new technique can reach the discriminating sensitivity of the immunologic techniques, since the existing convertase activity in plasma and on biomaterials is low, while it increases 2 to 5-fold after incubation of the biomaterial in plasma. Since the convertase remains active during substrate conversion, the development of the colour can be extended until discrimination between the test samples is possible. Another important aspect of the complement measurement on biomaterials with the presented in vitro technique is that substrate cleavage has been shown for human as well as various animal species (38,39).

Peptide substrates have been described in the past for the measurement of proteases. The synthesis of labeled substrates has been described (43). Most of the activated plasma proteases are highly specific when compared with digestive enzymes, such as trypsin or chymotrypsin. In some cases, the plasma proteases cleave only one or two peptide bonds in their natural substrates. This high enzyme specificity apparently is due to the recognition of a specific amino acid sequence near the sensitive bond or a specific conformation of these amino acids near the sensitive bond.

A number of studies of the effect of the various blood coagulation factors and complement enzymes have been published. Substrates containing 4-nitroaniline and amides of 7-amino-4-methylcoumarin have been particularly useful. None of these substrates, however, are completely specific. Other problems are the low rate of enzymatic hydrolysis and interference with other plasma proteins, such as albumin.

These disadvantages have made these substrate techniques for detection of complement activation in vivo difficult to interpret, since complement activation in vivo is accompanied by activation of other blood cascade systems with some effect on substrate conversion.

The methodology described in this document enables a high specificity, mainly due to the fact that the biocompatibility will be determined in vitro. In contrast to the measurements in blood samples from patients, during the in vitro measurement of biocompatibility, activation of cascades other than complement can be suppressed with commercially available inhibitors, allowing the process to be controlled (38). Moreover, complement convertases have the specific property to bind to the target biomaterial surface. Since the technique described herein is based on incubation of the test material in plasma followed by separation and washing of the test material, bound convertases on the material surface are separated from plasma prior to substrate conversion.

The present invention provides a technique to determine one important aspect of the biocompatibility from biomaterials, being the extent of complement activation. The present invention allows in vitro determination of complement activation by incubating biological fluids, blood or blood products with biomaterials, allowing the complement system to be activated and complement convertases to bind to the biomaterials surface. Subsequently, the biomaterials are washed to remove unbound blood proteins and cells and then the biomaterials are incubated in medium containing specific substrate, allowing cleavage of this substrate by complement convertases. This cleavage can then be measured due to release of colour, fluorochromes, radioactive label, etc.

In general, substrates in the present invention are labeled tripeptides, although larger structures are not limited hereby. The substrates have or comprise an amino acid sequence resembling the cleavage site of the natural substrate for the complement convertase or any other amino acid sequence with low Km and high specificity. The concentration of the substrate in the test procedure will normally be in the order of $\mu$M in order to have no substrate limitation during the test procedure.

Blood or blood plasma must be anticoagulated during incubation with the biomaterials. Some anticoagulants, such as the $Ca^{++}$ depleting agents citrate and EDTA, also affect the complement system. $Mg^{++}$ may be used in these situations to allow alternative pathway complement activation. More preferably, serum or fibrinogen depleted plasma or blood/plasma with specific thrombin inhibitors is used to prevent clotting during incubation with biomaterials.

A technique described in the present invention may be used in the screening of biomaterials to select the proper ones for construction of medical devices. It may also be used by test laboratories for blood biocompatibility testing. Further it may be used for research purposes during clinical use of medical devices or inversily to test the ability of an unknown blood sample to react with biomaterials.

The present invention also provides conditions to ensure specificity of the technique for complement convertases rather than other enzymes to cleave the substrates, by introduction of inhibitors for other enzymes during substrate conversion.

The present invention comprises measurement of complement activation both on the material surface and in the fluid phase. Dependent on the material surface, convertases are released in the biological fluid.

The present invention provides measurement of complement activation in human or animal biological fluid.

The present invention allows discrimination between activation of the alternative or classical pathway of the complement system, by employing $Ca^{++}$ or $Mg^{++}$ in the biological fluid during incubation with biomaterials, by means of heat treatment of the biological fluid or by inhibition of one of these pathways e.g. with antibodies.

The present invention enables measurement of complement convertase binding to biomaterials during clinical use of these biomaterials by incubation of these used and washed biomaterials in the substrate medium.

The present invention allows measurement of convertase activity with substrates labeled with chromophores or fluorogenes or other suitable markers which are released during peptide cleavage of substrate by the complement convertase.

The present invention provides the possibility to characterize complement activation by any device, independent of three-dimensional structure or size. If needed the incubation time with substrate can be adjusted to the number of convertases formed during incubation which might be dependent on the surface area and material characteristics of the test material.

The present invention can also be used to detect any deficiencies of the complement system to respond to standardized material with well defined characteristics with respect to complement activation. These standardized materials can be activators of the alternative or classical complement pathway. The advantage of this technique over the existing hemolytic or immunologic techniques is that screening for complement deficiency is possible without specialized laboratory techniques. The present invention can even be developed into a bedside monitoring of complement.

The present invention can be performed at varying temperatures, such as at room temperature or at 37° C., the main effect is the reaction speed.

The present invention allows a great extent of standardization for both the measurement of biocompatibility from biomaterials with pooled normal serum and for the measurement of complement response from patients plasma to standard biomaterials. For the biocompatibility measurement one batch of serum can be stored deep frozen in aliquots, for complement testing one batch of uniform material can be used.

The invention will be illustrated by the following examples which merely serve to illustrate the invention and not to limit it to the details shown. These examples demonstrate that we have evaluated a technique to detect the activation of the complement system, when a biomaterial is in contact with blood plasma. In our experiments it is shown that the biomaterial binds complement convertase and releases these convertases in plasma, which results in conversion of specific substrate. So activation of the complement system by biomaterials can now be measured directly in the fluid as well as on the surface.

In these experiments we have also shown that by means of this technique a classification can be made between different biomaterials with regard to the complement-biocompatibility. Therefore this test may become a powerful tool to access this biocompatibility of biomaterials in the selection and testing of materials to be used in medical devices.

EXAMPLE 1

Human blood was collected from a healthy volunteer by vena puncture. Blood was mixed immediately with sodium citrate (0.316%, final concentration) to prevent clotting. Then blood was centrifuged (1100 xg) to obtain separation between plasma and blood cells. In our experiments we used this citrated human plasma after treatment with reptilase to coagulate fibrinogen. This plasma, deficient of fibrinogen (def PPP), contains the other coagulation components and can be mixed with $Ca^{++}$ containing buffer to optimize complement activation. This def PPP was stored in aliquots at −80° C. We diluted this in 50 mM TRIS buffer+33 mM $CaCl_2$ (pH 7.4) to a percentage of 20% prior to use. The biomaterial PDMS (polydimethyl-siloxane, silicon rubber) was cut into 1 $cm^2$ pieces. For cleaning the biomaterial it was incubated at first in 70% ethanol, and then rinsed in 0.9% NaCl. During the experiment the pieces of biomaterials were incubated in 500 µl diluted def PPP during 0, 10, 30, or 60 min at room temperature. After incubation, the biomaterials were rinsed 3 times with saline. Then the biomaterials were incubated in BOC-Leu-Gly-Arg-pNA, diluted in TRIS buffer +33 mM $CaCl_2$, during 60 hours at room temperature in the dark. Simultaneously, also 100 µl def PPP, in which the biomaterials had been incubated, were mixed with 100 µl of H-Leu-Gly-Arg-pNA or Bz-Leu-Gly-Arg-pNA, diluted in TRIS buffer, supplemented with 33 mM $CaCl_2$. After these 60 hours the OD was measured at 405 nm in a spectrophotometer (microplate reader 3550 UV; Biorad, Richmond, Calif., USA).

These experiments showed colour formation releasing from PDMS with substrate BOC-Leu-Gly-Arg-pNA and in the incubated def PPP with substrates H-Leu-Gly-Arg-pNA and Bz-Leu-Gly-Arg-pNA (FIG. 3a).

Then, the effect of the incubation time of the biomaterial in plasma was investigated.

It is shown that substrate conversion, expressed as OD 405 nm, increases when the biomaterial is for a longer time in contact with plasma (FIG. 3b), indicating more C5-convertase formation. Since in this experiment after an incubation time of 30 min there was sufficient conversion, this incubation time was chosen in further experiments as a standard time.

EXAMPLE 2

To verify the specificity of complement convertase activity, PDMS was incubated with diluted def PPP supplemented with $Ca^{++}$ (allowing convertases to be formed) or with EDTA (preventing convertase formation). This experiment showed that EDTA completely prevented convertase formation, indicating some specificity of substrate for complement activation.

In a second experiment the incubated def PPP was incubated in the presence of $Ca^{++}$ as described above and 100 $\mu$l def PPP was collected after 30 minutes. Then this collected def PPP was incubated with H-Leu-Gly-Arg-pNA and Bz-Leu-Gly-Arg-pNA in the presence of $Ca^{++}$ or in the absence of $Ca^{++}$ with EDTA. The formed convertases remained active in EDTA, while additional convertase activity was formed in the presence of $Ca^{++}$ during the incubation of activated def PPP with substrate H-Leu-Gly-Arg-pNA (FIG. 4a). This neoformation of convertases can be considered as an artifact. Thus the second incubation of def PPP with substrate must be performed in $Ca^{++}/Mg^{++}$ chelating medium, like EDTA. Substrate Bz-Leu-Gly-Arg-pNA is considered non-specific for complement activation, since EDTA did not inhibit further cleavage of this substrate.

A third test for specificity was the incubation of PDMS with def PPP heated during 30 min at 56° C., in order to eliminate factor B from the alternative complement pathway. Under these conditions convertase formation was considerably reduced, indicating the importance of functional factor B from the alternative complement pathway in convertase formation by PDMS (FIG. 4b).

EXAMPLE 3

We have investigated the effect of different types of biomaterial, since discrimination between materials is one of the major goals of this technique.

We used the materials: PDMS, PE (polyethylene) and PTFE (polytetrafluoroethylene), which are all frequently used for medical devices. We have tested the effects of convertase formation in the solutions and onto the biomaterials. The materials PDMS, PE and PTFE activate the complement system, indicated by conversion of BOC-Leu-Gly-Arg-pNA and H-Leu-Gly-Arg-pNA (FIG. 5a,b). PDMS appeared a stronger activator than PE, whereas PTFE was a very weak activator of complement.

EXAMPLE 4

Figure 6:
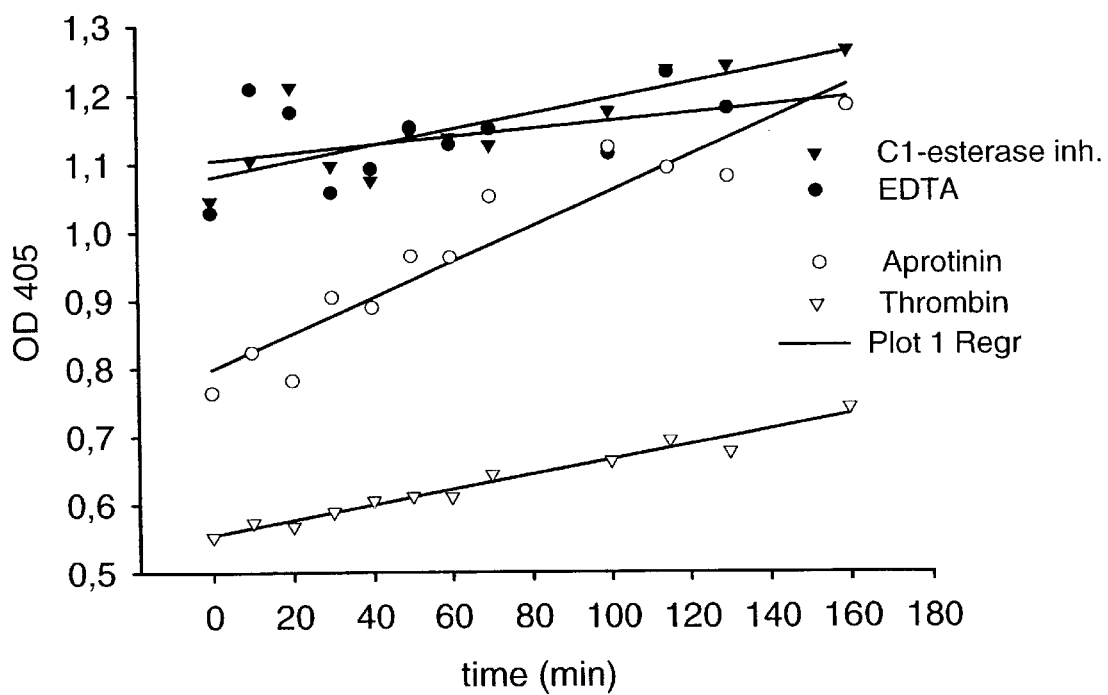
FIG. 6 shows the effect of various inhibitors during the incubation. PDMS was incubated in defibrinated plasma aliquots which differed by the inhibitors added prior to incubation, i.e., EDTA, aprotinin, C1-esterase inhibitor and thrombin inhibitor. EDTA almost completely prevented substrate conversion, aprotinin did not inhibit substrate conversion. This supports specificity of the substrate under these in vitro conditions for complement convertase activity, since aprotinin at the concentrations in this test inhibits kallikrein, plasmin, and (chymo)trypsin.

A number of enzyme inhibitors was used to further specify the complement convertase test of the incubated def PPP with substrate H-Leu-Gly-Arg-pNA. During incubation with PDMS in different aliquots a specific thrombin inhibitor (I2581, Kabi), C1 esterase inhibitor (Sigma), the plasmin/kallikrein/chymotrypsin inhibitor aprotinin (Bayer) and EDTA was used. EDTA was the best inhibitor, followed by C1-esterase inhibitor, then the thrombin inhibitor, then aprotinin (FIG. 6). This indicates that the main activity towards cleavage of the substage H-Leu-Gly-Arg-pNA is complement dependent.

REFERENCES

1) Knudsen, F, Nielsen AH, Pedersen JO, Jersild O. On the kinetics of complement activation leucopenia and granulocyte-elastase release induced by haemodialysis. Scand J Clin Lab Invest 45: 759–766, 1985
2) Aljama P, Bird PAE, Ward MK, Feest TG, Walker W, Tanboga H, Sussman M, Kerr DNS. Haemodialysis-induced leucopenia and activation of complement: Effects of different membranes. Proc Eur Dial Tr Assoc 15: 144–153
3) Boyce NW, Holdsworth SR. Evidence for direct renal injury as a consequence of glomerular complement activation. J Immunol 136: 2421–2425, 1986
4) Wegmüller E, Kazatchkine MD, Nydegger UE. Complement activation during extracorporeal blood bypass. Plasma Ther Transfus Technol 4: 361–371, 1983
5) Cheung AK, LeWinter M, Chenoweth DE, Lew WYW, Henderson LW, McLeod Bc, Viernes A, Sassetti RJ. Complement metabolism during membrane plasma separation. Artificial Organs 7: 443–449, 1983
6) Jacob HS. The role of activated complement and granulocytes in shock states and myocardial infarction. J Lab Clin Med 98: 645–653, 1981
7) Damerau B. Grüefeld E, Vogt W. Aggregation of leukocytes induced by the complement-derived peptides C3a and C5a and by three synthetic formyl-methionyl peptides. Int Archs Allergy Appl Immun 63: 159–169, 1980
8) Morgan EL, Thoman ML, Weigle WO, Hugli TE. Anaphylatoxin-mediated regulation of the immune response II, C5a-mediated enhancement of human humoral and T cell-mediated immune responses. J Immunol 130: 1257–1261, 1983
9) Janatova J, Gobel RJ. Activation of the third (C3) and the fourth (C4) components of complement: Generation and isolation of physiologically relevant fragments C3c and C4c. J Immunol Meth 85: 17–26, 1985
10) Pangburn MK, Schreiber RD, Müller-Eberhard HJ. C3b deposition during activation of the alternative complement pathway and the effect of deposition on the activating surface. J Immunol 130: 1930–1935, 1983
11) Law SK, Levine RP. Interaction between the third complement protein and cell surface macromolecules. Biochemistry 74: 2701–2705, 1977
12) Maillet F, Kazatchkine MD. Modulation of the formation of the human amplification C3 convertase of complement by polycations. J Immunol 50: 27–33, 1983
13) Janatova J, Tack BF, Prahl JW. Third component of human complement: structural requirements for its function. Biochemistry 19: 4479–4485, 1980
14) Pangburn MK, Müller-Eberhard HJ. Relation of a putative thioester bond in C3 to activation of the alternative pathway and the binding of C3b to biological targets of complement. J Exp Med 152: 1102–1114, 1980
15) Kazatchkine MD, Nydegger UE. The human alternative complement pathway: Biology and immunopathology of activation and regulation. Prog Allergy 30: 193–234, 1982
16) Ross, GC, Newman SL, Lambris JD, Devery-Pocius JE, Cain JA, Lachmann PJ. Generation of three different fragments of bound C3 with purified factor I or serum. Location of binding sites in the C3 fragments for factors B and H, complement receptors, and bovine conglutinin. J Exp Med 158: 334–352, 1983
17) Fishelson Z, Müller-Eberhard. Residual hemolytic and proteolytic activity expressed by Bb after decay-dissociation of C3b,Bb. J Immunol 132: 1425–1429, 1984
18) Daha Mr, Fearon DT, Austen KF. C3 Requirements for formation of alternative pathway C5 convertase. J Immunol 117: 630–634, 1976
19) Fischer E, Kazatchkine MD. Surface-dependent modulation by H of C5 cleavage by the cell-bound alternative pathway C5 convertase of human complement. J Immunol 130: 2821–2824, 1983
20) Alsenz J, Lambris JD, Schulz TF, Dierich MP. Localization of the complement component C3b binding site and the cofactor activity for factor I in the 38 kDa tryptic fragment of factor H. Biochem J 224: 389–398, 1984
21) Mantovani B. Different roles of IgG and complement receptors in phagocytosis by polymorphonuclear leukocytes. J Immunol 115: 15–17, 1975
22) Melamed J, Medicus RG, Arnaout MA, Colten HR. Induction of granulocyte of histaminase release by particle-bound complement C3 cleavage products (C3b, C3bi) and IgG. J Immunol 131: 439–444, 1983

23) Regal JF, Eastman Ay, Pickering RJ. C5a induced tracheal contraction: a histamine independent mechanism. J Immunol 124: 2876–2878, 1980

24) Wiedmer T, Esmon CT, Sims PJ. Complement proteins C5b-9 stimulate procoagulant activity through platelet prothrombinases. Blood 68: 875–880, 1986

25) Williams JJ, Yellin SA, Slotman GJ. Leukocyte aggregation response to quantitative plasma levels of C3a and C5a. Arch Surg 121: 305–307, 1986

26) Hammerschmidt DE, Bowers TK, Lammi-Keefe CJ, Jacob HS, Craddock PR. Granulocyte aggregometry: A sensitive technique for the detection of C5a and complement activation. Blood 55: 898–902, 1980

27) Yancey KB, Hammer CH, Harvath L, Renfer L, Frank MM, Lawley TJ. Studies of human C5a as a mediator of inflammation in normal human skin. J Clin Invest 75: 486–495, 1985

28) Roos D, Bot AAM, Schaik van LJ, Boer de M, Daha MR. Interaction between human neutrophils and zymosan particles: The role of opsonins and divalent cations. J Immunol 126: 433–440, 1981

29) Stossel TP, Field RJ, Gitlin JD, Alper CA, Rosen FS. The opsonic fragment of the third component of human complement (C3). J Exp Med 141: 1329–1345, 1975

30) Dijk van H, Rademaker PM, Willers JMN. Determination of alternative pathway of complement activity in mouse serum using rabbit erythrocytes. J Immunol Methods 36: 29–39, 1980

31) Tanaka S, Suzuki T, Nishioka K. Assay of classical and alternative pathway activities of murine complement using antibody-sensitized rabbit erythrocytes. J Immunol 86: 161–170, 1986

32) van Oeveren W, Kazatchkine MD, Descamps Latscha B. Deleterious effects of cardiopulmonary bypass. J Thorac Cardiovasc Surg 89: 888–889, 1985

33) Hugli TE, Chenoweth DE. Biologically active peptides of complement: Techniques and significance of C3a and C5a measurements. Immunoassays clinical laboratory techniques 443–460, 1980

34) Gorski JP. Quantitation of human complement fragment C4ai in physiological fluids by competitive inhibition radioimmune assay. J Immunol Meth 47: 61–73, 1981

35) Linder E, Rhen M, Meri S. An immunofluorescence assay for complement activation by the classical pathway. J Immunol Meth 47: 49–59, 1981

36) Burger R, Zilow G, Bader A, Friedlein A, Naser W. The C terminus of the anaphylatoxin C3a generated upon complement activation represents a neoantigenic determinant with diagnostic potential. J Immunol 141: 553–558, 1988

37) Chenoweth DE, Cooper SW, Hugli TE, Steward RW, Blackstone EH, Kirklin JW. Complement activation during cardiopulmonary bypass. Evidence for generation of C3a and C5a anaphylatoxins. N Engl J Med 304: 497–502, 1981

38) Bhakdi S, Tranum-Jensen J. Membrane damage by complement. Biochim Biophys Acta 737: 343–372, 1983

39) Wiman B, Nilson T. A new simple method for determination of C1-esterase inhibitor activity in plasma. Clinica Chimica Acta 128: 359–366, 1983

40) Carporale LH, Gaber SS, Kell W, Götze O. A fluorescent assay for complement activation . J Immunol 126: 1963–1965, 1981

41) Bharadwaj D, Roy MS, Bose D, Hati RN. A new blood-coagulation protease in mitochondrial membranes of rat submaximillary glands. J Biol Chem 269: 16229–16235, 1994

42) Higuchi K, Kajiki A, Nakamura M, Harada S, Pula PJ, Scott AL, Dannenberg AM. Proteases released in organ culture by acute dermal inflammatory lesions produced in vivo in rabbit skin by sulfur mustard. Inflammation 12: 311–334, 1988

43) Tack BF, Janatova J, Thomas ML, Harrison RA, Hammer CH. The third, fourth, and fifth components of human complement: isolation and biochemical properties. Meth Enzymol 80: 64–101, 1981

44) Kerr MA. Human Factor B. Meth Enzymol 80: 102–112, 1981

45) Kem CM, McRae BJ, Harper JW, Niemann MA, Volonakis JE, Powers JC. Human complement proteins D, C2, and B. J Biol Chem 262: 3444–3451, 1987

46) McRae BJ, Kurachi K, Heimark RL, Fujikawa K, Davie EW, Powers JC. Mapping the active sites of bovine thrombin, Factor IXa, Factor Xa, Factor XIa, Factor XIIa, plasma kallikrein, and trypsin with amino acid and peptide thioesters: development of new sensitive substrates. Biochemistry 20: 7196–7206, 1981

We claim:

1. A process for determining complement activation due to contact between a biomaterial and a complement system, comprising incubating in vitro the biomaterial with the complement system and determining the formation of a complement convertase by using a substrate of the complement convertase and detecting cleavage of said substrate.

2. A process as claimed in claim 1, wherein the biomaterial is separated from the complement system, after said incubating, to provide a biomaterial fraction and a complement system fraction, both fractions having complement convertase activity, and wherein the determining of the formation of complement convertase is carried out with the biomaterial fraction, the complement system fraction, or both.

3. A process as claimed in claim 1, wherein said complement convertase is selected from the group consisting of Factor B convertase, C3 convertase and C5 convertase.

4. A process as claimed in claim 1, wherein said complement convertase is C5 convertase.

5. A process as claimed in claim 1, wherein said complement convertase substrate is a labeled oligopeptide comprising an amino acid sequence corresponding to the cleavage site of the complement convertase.

6. A process as claimed in claim 5, wherein said labeled oligopeptide is a labeled tripeptide is selected from the group of peptides consisting of Leu-Gly-Arg-Label, Leu-Ala-Arg-Label, and Gln-Lys-Arg-Label, wherein the label and the terminal amino group of the N-terminal amino acid may be blocked.

7. A process as claimed in claim 5, wherein the label in said labeled oligopeptide is selected from the group consisting of dyes, fluorochromes, radioactive atoms or groups, and enzymes.

8. A process as claimed in claim 1, wherein either classical pathway complement activation, alternative pathway complement activation, or both, are determined.

9. A process as claimed in claim 1, wherein said complement system is a non-clotting derivative of blood, blood plasma or blood serum.

10. A process as claimed in claim 1, wherein the interference by other enzymes than the complement convertase is reduced by carrying out the incubation of biomaterial and complement system and/or the substrate cleavage step in the presence of inhibitors of said other enzymes.

11. A process as claimed in claim 1 to determine the complement activating properties of a biomaterial, wherein said complement system is derived from blood known to have an active classical pathway complement system, an active alternative pathway complement system, or both.

12. A process as claimed in claim 1 to determine the complement response properties of a complement system, wherein biomaterials with known complement activating properties are used.

* * * * *